(12) United States Patent
Nagasawa et al.

(10) Patent No.: US 6,197,970 B1
(45) Date of Patent: Mar. 6, 2001

(54) PROCESS FOR PRODUCING 2-HYDROXYBENZAMIDE DERIVATIVES

(75) Inventors: Masaaki Nagasawa; Hiroyasu Nishioka, both of Osato-gun; Takanori Suzuki, Konan-machi; Eiichi Nagano, Konan-machi; Katsuyuki Ishii, Konan-machi; Ryu Nakao, Konan-machi, all of (JP)

(73) Assignee: Zeria Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/446,108
(22) PCT Filed: Jun. 22, 1998
(86) PCT No.: PCT/JP98/02764
    § 371 Date: Dec. 23, 1999
    § 102(e) Date: Dec. 23, 1999
(87) PCT Pub. No.: WO98/58918
    PCT Pub. Date: Dec. 30, 1998

(30) Foreign Application Priority Data

Jun. 24, 1997 (JP) .................................. 9-181844
Sep. 1, 1997 (JP) .................................. 9-250106

(51) Int. Cl.[7] .............................................. C07D 277/56
(52) U.S. Cl. ................................................... 548/195
(58) Field of Search ........................................... 548/195

(56) References Cited

U.S. PATENT DOCUMENTS 5,981,557  11/1999  Nagasawa et al. .

OTHER PUBLICATIONS

Lancaster Catalog p. 496 #1936 (2,4,6–Collidine), 1999.*

* cited by examiner

*Primary Examiner*—Robert Gerstl
(74) *Attorney, Agent, or Firm*—Oblon, Spivak, McClelland, Maier & Neustadt, P.C.

(57) ABSTRACT

The present invention is directed to a process for producing 2-hydroxybenzamide derivatives (2) or (5) according to either one of the following reaction schemes.

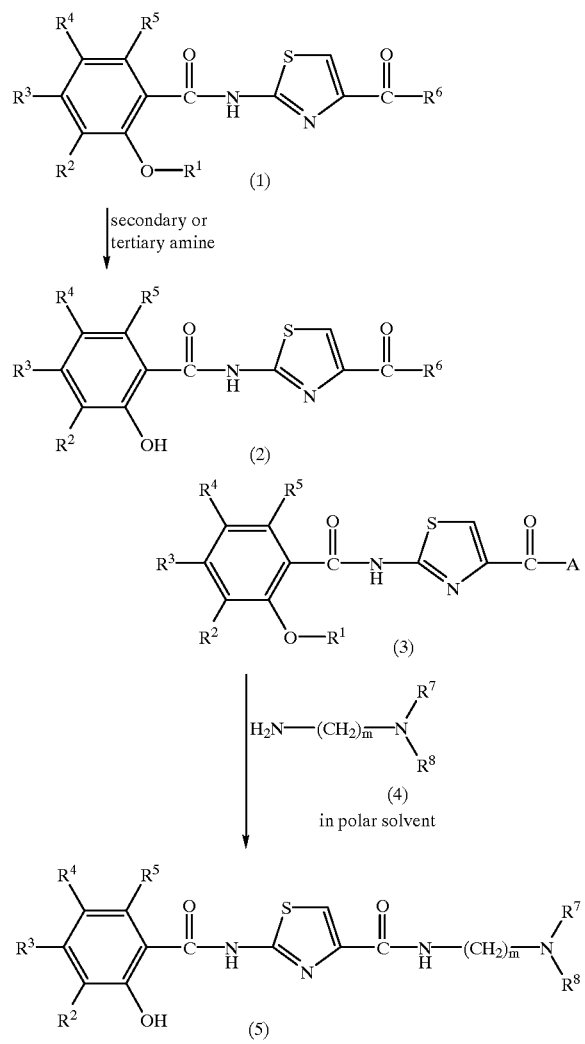

8 Claims, No Drawings

PROCESS FOR PRODUCING 2-HYDROXYBENZAMIDE DERIVATIVES

TECHNICAL FIELD

The present invention relates to a process for producing 2-hydroxybenzamide derivatives which are useful as pharmaceuticals or intermediate products.

BACKGROUND ART

2-Hydroxybenzoylaminothiazole derivatives having a hydroxy group at the 2-position on the benzene ring are known to have effects for the improvement of gastrointestinal dysmotility, which makes them useful as preventive or therapeutic drugs for various types of gastrointestinal dysmotility (WO96/36619). Among such 2-hydroxybenzoylaminothiazole derivatives, 2-[N-(4,5-dimethoxy-2-hydroxybenzoyl)amino]-4-[(2-diisopropylaminoethyl)aminocarbonyl]-1,3-thiazole has particularly excellent effects for the improvement of gastrointestinal dysmotility and thus is useful as a pharmaceutical.

According to the descriptions of the above-described WO96/36619, the 2-hydroxybenzoylaminothiazole derivative is produced through the following procedure. 2-Hydroxybenzoic acid serving as a raw material is subjected to condensation reaction with 2-amino-4-alkoxycarbonyl-1,3-thiazole (step 1). Subsequently, the alkoxycarbonyl group of the thiazole ring is further subjected to amidation (step 2).

However, when the carboxy group of 2-hydroxybenzoic acid is activated by use of a condensing agent or a halogenating agent so as to perform the above-described step 1 reaction, reaction such as polymerization frequently occurs, so make production of the target product difficult. To avoid this problem, a conceivable method in the case of amidation of 2-hydroxybenzoic acid (step 1) is as follows. The hydroxy group at the 2-position of the benzene ring of 2-hydroxybenzoic acid (hereinafter referred to as "the 2-hydroxy group") is protected and then reacted with a compound having an amino group, after which, deprotection is performed. Examples of the protective group for the 2-hydroxy group used in the present method include known protective groups such as an alkyl group, an allyl group, a benzyl group, a tetrahydropyranyl group, and a silyl group. Of these, an alkyl group is generally used. For deprotection, a known dealkylation reaction may be performed (conversion of an alkoxy group into a 2-hydroxy group). Examples of known dealkylation reactions include those by use of acidic reagents including Brønsted acids such as hydrobromic acid, hydriodic acid, and trifluoroacetic acid, Lewis acids such as boron tribromide and aluminum chloride (frequently used singly or in combination with alkyl sulfurs), pyridine hydrochloride, and hydrobromic acid-acetic acid solution; reactions by use of alkaline reagents such as sodium methoxide, sodium cyanide, lithium diphenylphosphine, and lithium chloride; reactions by use of silicon reagents such as trimethylsilyl iodide; and hydrogenation reduction such as catalytic reduction.

However, through these known deprotection reactions, selective dealkylation at the 2-position is difficult for a compound having a substituent such as an alkoxy group or an ester group at a position other than the hydroxy-protected 2-position of the benzene ring at which hydroxy is protected (hereinafter referred to as "the 2-protected hydroxy group"). In addition, particularly in the case of a reaction by use of an alkaline reagent, solvolysis and a side reaction attributable to a base may occur, and, when there is employed an N-thiazolyl-2-substituted benzamide compound containing a catalyst poison such as sulfur atoms in the substrate, hydrogenation reduction cannot be completed. Therefore, there is still need for a process for efficiently producing a 2-hydroxybenzamide derivative, in which the 2-protected hydroxy group is selectively dealkylated without affecting other substituents on the benzene ring and without causing any side reaction.

DISCLOSURE OF THE INVENTION

In view of the foregoing, the present inventors have performed earnest studies on a process for producing a 2-hydroxybenzamide derivative, and have found that when a 2-substituted benzamide compound obtained from the reaction between 2-substituted benzoic acid and a compound having an amino group is reacted with a secondary amine or a tertiary amine, the 2-protected hydroxy group is selectively deprotected and converted into a hydroxy group with other substituents on the benzene ring being not affected—and if there are substituents on locations other than the benzene ring, such substituents also being not affected—or without causing any side reaction. They have also found that when the 2-substituted benzamide compound is reacted with a primary amine in the presence of a polar solvent, deprotection of the 2-protected hydroxy group and amidation proceed in parallel, to thereby industrially and advantageously produce a useful compound serving as the above-described preventive and therapeutic drug for gastrointestinal dysmotility. The present invention has been accomplished based on these findings.

Accordingly, the present invention provides a process for producing a 2-hydroxybenzamide derivative represented by formula (2):

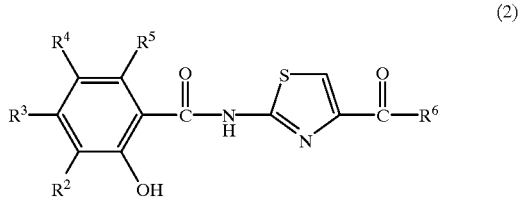

(2)

wherein $R^2$, $R^3$, and $R^4$ are the same or different and each independently represents a hydrogen atom, a hydroxy group, a lower alkyl group, a lower alkoxy group, a lower alkylsulfonyl group, a halogen atom, a nitro group, a cyano group, a mono- or di-lower alkylamino group, or a mono- or di-lower alkylcarbonylamino group, or $R^2$ and $R^3$ may join to each other to form a methylenedioxy group; $R^5$ represents a hydrogen atom, a lower alkyl group, a lower alkylsulfonyl group, a halogen atom, a nitro group, a cyano group, a mono- or di-lower alkylamino group, or a mono- or di-lower alkylcarbonylamino group; and $R^6$ represents a hydroxy group, a lower alkyl group, or a lower alkoxy group; which process is characterized by reacting a 2-substituted benzamide compound represented by formula (1):

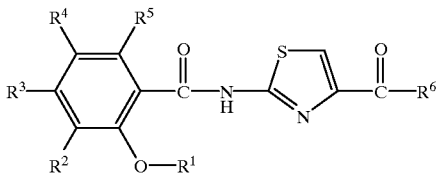

(1)

wherein $R^1$ represents a substituted or unsubstituted lower alkyl group, a substituted or unsubstituted allyl group, a substituted or unsubstituted benzyl group, or a substituted or unsubstituted tetrahydropyranyl group; and $R^2$, $R^3$, $R^4$, $R^5$, and $R^6$ have the same meanings as described above; with a secondary amine or a tertiary amine.

The present invention also provides a process for producing a 2-hydroxybenzamide derivative represented by formula (5):

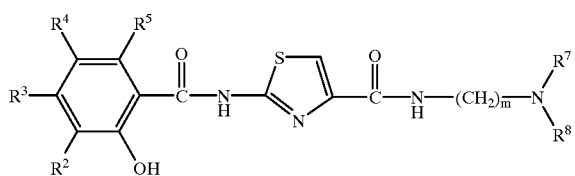

(5)

wherein $R^2$, $R^3$, $R^4$, $R^5$ have the same meanings as described above; $R^7$ and $R^8$ are the same or different and each independently represents a hydrogen atom or a lower alkyl group; and m represents an integer of 1–4 inclusive, which process is characterized by reacting a 2-substituted benzamide compound represented by formula (3):

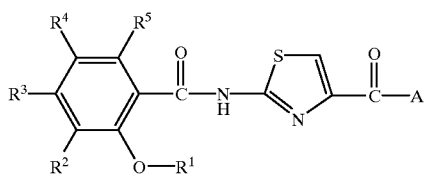

(3)

wherein A represents a hydroxy group or a lower alkoxy group and $R^1$, $R^2$, $R^3$, $R^4$, and $R^5$ have the same meanings as described above with a primary amine represented by formula (4):

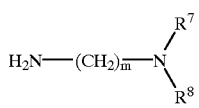

(4)

wherein m, $R^7$, and $R^8$ have the same meanings as described above, in the presence of a polar solvent.

BEST MODE FOR CARRYING OUT THE INVENTION

In the present invention, the term "lower" means a linear, branched, or cyclic carbon chain having 1 to 6 carbon atoms.

Accordingly, the term "lower alkyl group" refers to linear, branched, or cyclic alkyl groups having 1 to 6 carbon atoms. Specific examples of such alkyl groups include methyl, ethyl, propyl, isopropyl, cyclopropyl, butyl, isobutyl, sec-butyl, tert-butyl, cyclobutyl, pentyl, 1-methylbutyl, 2-methylbutyl, isopentyl, tert-pentyl, 1,2-dimethylpropyl, neopentyl, 1-ethylpropyl, cyclopentyl, hexyl, 1-methylpentyl, 2-methylpentyl, 3-methylpentyl, isohexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methyl-1-ethylpropyl, 1-ethyl-2-methylpropyl, 1,1,2-trimethylpropyl, 1,2,2-trimethylpropyl, and cyclohexyl. Among these, linear or branched alkyl groups having 1 to 4 carbon atoms are more preferred.

The term "lower alkoxy group" refers to linear, branched, or cyclic alkoxy groups having 1 to 6 carbon atoms. Specific examples of such alkoxy groups include methoxy, ethoxy, propoxy, cyclopropoxy, isopropoxy, butoxy, isobutoxy, sec-butoxy, tert-butoxy, cyclobutoxy, pentyloxy, 1-methylbutoxy, 2-methylbutoxy, isopentyloxy, tert-pentyloxy, 1,2-dimethylpropoxy, neopentyloxy, 1-ethylpropoxy, cyclopentyloxy, hexyloxy, 1-methylpentyloxy, 2-methylpentyloxy, 3-methylpentyloxy, isohexyloxy, 1-ethylbutoxy, 2-ethylbutoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-methyl-1-ethylpropoxy, 1-ethyl-2-methylpropoxy, 1,1,2-trimethylpropoxy, 1,2,2-trimethylpropoxy, and cyclohexyloxy. Among these, linear or branched alkoxy groups having 1 to 4 carbon atoms are more preferred.

In formula (1), the term "a substituted or unsubstituted lower alkyl group, a substituted or unsubstituted allyl group, a substituted or unsubstituted benzyl group, or a substituted or unsubstituted tetrahydropyranyl group" refers to the above-described lower alkyl group itself or a lower alkyl group having one or more substituents, an allyl group itself or an allyl group having one or more substituents, a benzyl group itself or a benzyl group having one or more substituents, or a tetrahydropyranyl group itself or a tetrahydropyranyl group having one or more substituents. Any alkyl, allyl, benzyl, or tetrahydropyranyl group can be used so long as such a group can be removed through reaction of the present invention, and among them, the above-described lower alkyl group itself is preferably used.

The substituent group referred to in "a substituted or unsubstituted lower alkyl group, a substituted or unsubstituted allyl group, a substituted or unsubstituted benzyl group, or a substituted or unsubstituted tetrahydropyranyl group" may be any group so long as it is advantageously used in the reaction of the present invention. Specific examples of such a group include the above-described lower alkyl group itself, the above-described lower alkoxy group, a nitro group, and a hydroxy group.

In the present invention, the term "halogen atom" refers to fluorine, chlorine, bromine, and iodine.

The term "lower alkylsulfonyl group" refers to linear, branched, or cyclic alkylsulfonyl groups having 1 to 6 carbon atoms. Specific examples of such groups include methylsulfonyl, ethylsulfonyl, propylsulfonyl, isopropylsulfonyl, butylsulfonyl, isobutylsulfonyl, sec-butylsulfonyl, and tert-butylsulfonyl groups.

The term "mono- or di-lower alkylamino group" refers to amino groups substituted with one or two linear, branched, or cyclic alkyl groups having 1 to 6 carbon atoms. Specific examples of such groups include methylamino, ethylamino, propylamino, isopropylamino, cyclopropylamino, butylamino, isobutylamino, sec-butylamino, tert-butylamino, cyclobutylamino, pentylamino, 1-methylbutylamino, 2-methylbutylamino, isopentylamino, tert-pentylamino, 1,2-dimethylpropylamino, neopentylamino, 1-ethylpropylamino, cyclopentylamino, hexylamino, 1-methylpentylamino, 2-methylpentylamino, 3-methylpentylamino, isohexylamino, 1-ethylbutylamino, 2-ethylbutylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-methyl-1-ethylpropylamino, 1-ethyl-2-methylpropylamino, 1,1,2-trimethylpropylamino, 1,2,2-trimethylpropylamino, cyclohexylamino, dimethylamino, diethylamino, dipropylamino, diisopropylamino, dibutylamino, diisobutylamino, methylethylamino, methylpropylamino, methylisopropylamino, methylbutylamino, methylisobutylamino, methyl-sec-butylamino, methyl-tert-butylamino, methylcyclobutylamino, methylpentylamino, methylcyclopentylamino, methylhexylamino, ethylpropylamino, ethylisopropylamino, ethylbutylamino, ethylisobutylamino, ethyl-sec-butylamino, ethyl-tert-butylamino, ethylcyclobutylamino, ethylpentylamino, ethylneopentylamino, ethylcyclohexylamino, propylisopropylamino, propylbutylamino, propylisobutylamino, propyl-sec-butylamino, propyl-tert-butylamino, propylcyclobutylamino, propylpentylamino, propylisopentylamino, propyl-tert-pentylamino, propylcyclohexylamino, isopropylbutylamino, isopropylisobutylamino, isopropyl-sec-butylamino, isopropylpentylamino, butylisobutylamino, butyl-sec-butylamino, butyl-tert-butylamino, butylcyclobutylamino, butylpentylamino, butylisopentylamino, butyl-tert-pentylamino, butylneopentylamino, butyl(1-ethyl) propylamino, butylcyclopentylamino, butylhexylamino, butylisohexylamino, butylcyclohexylamino, isobutyl-sec-butylamino, isobutylpentylamino, isobutylisopentylamino, isobutylneopentylamino, isobutylhexylamino, isobutylisohexylamino, sec-butylisopentylamino, sec-butylneopentylamino, sec-butylhexylamino, tert-butylpentylamino, tert-butylisopentylamino, tert-butylhexylamino, cyclobutylpentylamino, cyclobutylisopentylamino, cyclobutylhexylamino, cyclobutylisohexylamino, pentylneopentylamino, pentylcyclopentylamino, pentylhexylamino, pentylisohexylamino, pentylcyclohexylamino, and isohexylcyclohexylamino. Among these, amino groups substituted with one or two linear or branched alkyl groups having 1 to 4 carbon atoms are most preferred.

The term "mono- or di-lower alkylcarbonylamino group" refers to amino groups substituted with one or two linear, branched, or cyclic alkylcarbonyl groups having 2 to 7 carbon atoms. Specific examples of such groups include acetylamino, propionylamino, butyrylamino, isobutyrylamino, cyclopropylcarbonylamino, valerylamino, isovalerylamino, sec-butylcarbonylamino, pivaloylamino, cyclobutylcarbonylamino, pentylcarbonylamino, 1-methylbutylcarbonylamino, 2-methylbutylcarbonylamino, isopentylcarbonylamino, tert-pentylcarbonylamino, 1,2-dimethylpropylcarbonylamino, neopentylcarbonylamino, 1-ethylpropylcarbonylamino, cyclopentylcarbonylamino, hexylcarbonylamino, 1-methylpentylcarbonylamino, 2-methylpentylcarbonylamino, 3-methylpentylcarbonylamino, isohexylcarbonylamino, 1-ethylbutylcarbonylamino, 2-ethylbutylcarbonylamino, 1,1-dimethylbutylcarbonylamino, 1,2-dimethylbutylcarbonylamino, 1,3-dimethylbutylcarbonylamino, 2,2-dimethylbutylcarbonylamino, 2,3-dimethylbutylcarbonylamino, 3,3-dimethylbutylcarbonylamino, 1-methyl-1-ethylpropylcarbonylamino, 1-ethyl-2-methylpropylcarbonylamino, 1,1,2-trimethylpropylcarbonylamino, 1,2,2-trimethylpropylcarbonylamino, cyclohexylcarbonylamino, diacetylamino, dipropionylamino, dibutyrylamino, diisobutyrylamino, divalerylamino, diisovalerylamino, acetylpropionylamino, acetylbutyrylamino, acetylisobutyrylamino, acetylvalerylamino, propionylbutyrylamino, propionylisobutyrylamino, propionylvalerylamino, butyrylisobutyrylamino, butyrylvalerylamino, and isobutyrylvalerylamino. Among these, amino groups substituted with one or two linear or branched alkyl groups having 2 to 5 carbon atoms are preferably used.

Any secondary amine or tertiary amine may be used for producing a compound represented by formula (2), so long as it does not affect other substituents present on 2-substituted benzamide compound (1). For example, there may be used a secondary or tertiary amine having an amino group to which a linear, branched, or cyclic alkyl group is bonded. Specific examples of such amines include N,N-di(lower alkyl)amine, N,N,N-tri(lower alkyl)amine, N-(lower alkyl)-N-[N'-(lower alkyl)aminoalkyl]amine, N-(lower alkyl)-N-[N',N'-di(lower alkyl)aminoalkyl]amine, N,N-di[N'-(lower alkyl)aminoalkyl]amine, N,N-di[N',N'-di(lower alkyl)aminoalkyl]amine, N-[N'-(lower alkyl)aminoalkyl]-N-[N',N'-di(lower alkyl)aminoalkyl]amine, N,N,N-tri[N'-(lower alkyl)aminoalkyl]amine, and N,N,N-tri[N',N'-di(lower alkyl)aminoalkyl]amine.

The reaction of the 2-substituted benzamide compound (1) with a secondary or teriary amine is typically carried out in the presence or absence of a solvent in a temperature range from room temperature to reflux temperature, preferably from 120° C. to reflux temperature. The solvent is suitably chosen from among known ones, and a mixture of 2 or more species of solvents may be used as needed. Preferred solvents are those having a boiling point of 120° C. or more. Among them, polar solvents are especially preferable, and amide-type or sulfoxide-type solvents such as N,N-dimethylformamide, N,N-dimethylacetamide, and dimethylsulfoxide or mixtures thereof are most preferred. After completion of reaction, the target compound is isolated and purified through customary chemical procedures such as filtration, washing, crystallization, recrystallization, and extraction. If desired, solvates or organic-acid- or inorganic-acid-addition salts may be prepared.

As described above, through reaction between the 2-substituted benzamide compound (1) and a secondary amine or tertiary amine, even when the compound (1) having an ester or alkoxy group (which may be the same as the 2-protected hydroxy group) other than the 2-protected hydroxy group is used, the amine selectively reacts with the 2-protected hydroxy group for deprotection and does not react with other substituents. Therefore, even in the presence of a substitutent such as an ester or alkoxy group—which are affected by conventional dealkylation—the target 2-hydroxybenzamide derivative (2) can be produced selectively at high yield.

According to the process described in the aforementioned WO96/36619, the compound of formula (5) may be produced from the 2-hydroxybenzamide derivative (2).

A polar solvent used in the reaction between the compound of formula (3) and the primary amine of formula (4)

may be appropriately chosen from known solvents. Examples of polar solvents include solvents having a boiling point of 120° C. or more, and of these, sulfoxide-type solvents such as dimethylsulfoxide and amide-type solvents such as N,N-dimethylsulfoxide and N,N-dimethylacetamide are preferred. These polar solvents may be used as mixtures at arbitrarily ratios. No particular limitation is imposed on the reaction temperature. Preferably, the reaction is performed with heat, particularly at a temperature of 120° C. or more. After completion of reaction, the reaction mixture is appropriately subjected to customary chemical procedures, including filtration, washing, crystallization, recrystallization, and extraction, to thereby isolate and purify the compound. If desired, by producing an acid-addition salt of organic or inorganic acid, or a solvate of the thus-obtained compound, the target compound of formula (5) may be produced.

According to the process of the present invention, deprotection of a 2-protected hydroxy group and amidation proceed simultaneously, and therefore the production steps may be simplified as compared with the process described in the aforementioned international patent publication or combinations of known reactions. In addition, since no side reactions are involved, the process of the present invention advantageously provides a high purity target compound at high yield.

EXAMPLES

The present invention will next be described in more detail by way of examples, which should not be construed as limiting the invention thereto.

Example 1

A suspension (30 ml) of 2-[N-(2,4,5-trimethoxybenzoyl) amino]-4-(ethoxycarbonyl)-1,3-thiazole (10.0 g) in N,N-dimethylacetamide was allowed to dissolve with heat at a temperature of at least 150° C., and di-n-butylamine (8.8 g) was added dropwise to the solution, refluxed for 5 hours. The reaction mixture was allowed to cool, poured into a mixture of 1 N hydrochloric acid (100 ml) and ice water (100 ml), and further, water was added thereto. The crystals so precipitated were collected by filtration, washed with water, and then subjected to air drying and drying under reduced pressure to thereby obtain crude crystals (10.0 g). The crystals were followed by recrystallization from 1,4-dioxane, thereby 8.9 g of 2-[N-(4,5-dimethoxy-2-hydroxybenzoyl)amino]-4-(ethoxycarbonyl)-1,3-thiazole was obtained (yield: 82.3%).

melting point: 218–220° C.

$^1$H-NMR(DMSO-d$_6$) δ: 1.31(3H, t), 3.57(4H, s), 3.78(3H, s), 3.83(3H, s), 4.30(2H, q), 6.61 (1H, s), 7.65(1H, s), 8.12(1H, s), 11.75(1H, s), 12.42(1H, s).

IR(KBr)cm$^{-1}$: 3229, 3113, 1728, 1643, 1556, 1518, 1273, 1232, 1213

Example 2

A suspension (6 ml) of 2-[N-(2,4,5-trimethoxybenzoyl) amino]-4-(ethoxycarbonyl)-1,3-thiazole (3.0 g) in dimethyl sulfoxide was dissolved with heat, and N-methyl-N-hexylamine (2.3 g) was added dropwise to the solution, refluxed for 2 hours. The reaction mixture was allowed to cool, poured into a mixture of 1 N hydrochloric acid (30 ml) and ice water (30 ml), and further, water was added thereto. Crystals so precipitated were collected by filtration, washed with water, and air-dried to thereby obtain crude crystals. The crystals were followed by recrystallization from 1,4-dioxane, 2.1 g of 2-[N-(4,5-dimethoxy-2-hydroxybenzoyl) amino]-4-(ethoxycarbonyl)-1,3-thiazole was obtained (yield: 64.6%).

Example 3

A suspension (1.5 ml) of 2-[N-(2,4,5-trimethoxybenzoyl) amino]-4-(ethoxycarbonyl)-1,3-thiazole (732 mg) and N,N-diisopropyl-N'-methylethylenediamine (1.60 g) in dimethylacetamide was stirred at 140° C. for 5 hours. To the reaction mixture, an aqueous solution of potassium hydrogensulfate, a small quantity of ethyl acetate, and a small quantity of isopropyl ether were added for precipitation of crystals. Crystals so precipitated were collected by filtration and dried to thereby obtain 601 mg of 2-[N-4,5-dimethoxy-2-hydroxybenzoyl)amino]-4-(ethoxycarbonyl)-1,3-thiazole (yield: 86%).

Example 4

Preparation of 2-[N-(4,5-dimethoxy-2-hydroxybenzoyl)amino]-4-[(2-diisopropylaminoethyl)aminocarbonyl]-1,3-thiazole hydrochloride Step 1

Preparation of 2-[N-(2,4,5-trimethoxybenzoyl) amino]-4-methoxycarbonyl-1,3-thiazole 2,4,5-Trimethoxybenzoic acid (500 g) was suspended in dried toluene (2 l) and to the suspension, thionyl chloride (206 ml) and N,N-dimethylformamide (1.0 ml) were added at room temperature, and the mixture was stirred at 80° C. for 1 hour. The reaction mixture was concentrated under reduced pressure. To the resultant residue, n-hexane was added and through co-boiling the mixture, 2,4,5-trimethoxybenzoyl chloride was obtained. To the resultant compound, 2-amino-4-methoxycarbonyl-1,3-thiazole (372.7 g) and 1,2-dichloroethane (4.5 l) were added and the mixture was refluxed for 6 hours. After completion of reaction, the reaction mixture was allowed to cool. Crystals so precipitated were collected by filtration, washed with 1,2-dichloroethane, and air-dried. The crystals were suspended in water (8 l) and to the suspension, ice (2 kg) was added. While cooling, a solution of sodium hydroxide (94 g) in water (850 ml) was added thereto to thereby adjust the pH of the suspension at about 7.5. Subsequently, the mixture was stirred for 3 hours at room temperature. Crystals so precipitated were collected by filtration, washed with water, and air-dried to thereby obtain the title compound (702.7 g).

melting point: 251–252° C.

$^1$H-NMR(DMSO-d$_6$) δ: 3.77(3H, s), 3.82(3H, s), 3.91 (3H, s), 4.03(3H, s), 6.84(1H, s), 7.44(1H, s), 8.04(1H, s), 11.44(1H, s)

IR(KBr) cm$^{-1}$: 3304, 3123, 3019, 1736, 1668, 1610

MS(FAB)m/e : 353(MH$^+$)

Step 2

Preparation of 2-[N-(4,5-dimethoxy-2-hydroxybenzoyl)amino]-4-[(2-diisopropylaminoethyl)aminocarbonyl]-1,3-thiazole hydrochloride Under argon atmosphere, 2-[N-(2,4,5-trimethoxybenzoyl) amino]-4-methoxycarbonyl-1,3-thiazole (500 g) and N,N-diisopropylethylenediamine (617 ml) were suspended in N,N-dimethylacetamide (617 ml) and the suspension was stirred at 135° C. for 6 hours. The reaction mixture was allowed to cool and 1-butanol (5 l) was added thereto. The mixture was successively washed with 0.5 N aqueous sodium hydroxide and saturated brine and 2-propanol (2 l) was added to the mixture. Hydrochloric acid gas was blown into the reaction mixture under ice-cooling until the liquid became acidic. Crystals so precipitated were collected by filtration and air-dried. The crystals were recrystallized from a mixed solvent of 2-propanol and water (2-propanol:water= 4:1) and 468.3 g of the title compound was obtained.

melting point: 160° C.

$^1$H-NMR(DMSO-d$_6$) δ: 1.32(6H, d), 1.35(6H, d), 3.17 (2H, brs), 3.55–3.70(4H, m), 3.77(3H, s), 3.82(3H, s), 6.87(1H, s), 7.49(1H, s), 7.89(1H, s), 8.23(1H, t), 9.65(1H, brs), 11.79(1H, s), 12.07(1H, brs)

IR(KBr) cm$^{-1}$: 3493, 3300, 3096, 1649

MS(FAB)m/e : 451(MH$^+$)

Industrial Applicability

The process of the present invention provides 2-hydroxybenzoylaminothiazole derivatives by a simple procedure at high yield as compared with conventional methods, and thus is industrially advantageous due to its excellent working efficiency and economy.

What is claimed is:

1. A process for producing a 2-hydroxybenzamide derivative represented by formula (2):

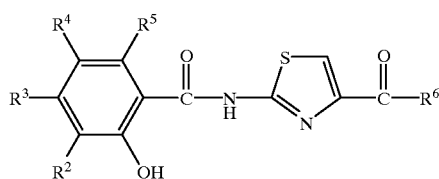

(2)

wherein R$^2$, R$^3$, and R$^4$ are the same or different and each independently represents a hydrogen atom, a hydroxy group, a lower alkyl group, a lower alkoxy group, a lower alkylsulfonyl group, a halogen atom, a nitro group, a cyano group, a mono- or di-lower alkylamino group, or a mono- or di-lower alkylcarbonylamino group, or R$^2$ and R$^3$ may join to each other to form a methylenedioxy group; R$^5$ represents a hydrogen atom, a lower alkyl group, a lower alkylsulfonyl group, a halogen atom, a nitro group, a cyano group, a mono- or di-lower alkylamino group, or a mono- or di-lower alkylcarbonylamino group; and R$^6$ represents a hydroxy group, a lower alkyl group, or a lower alkoxy group; which comprises reacting a 2-substituted benzamide compound represented by formula (1):

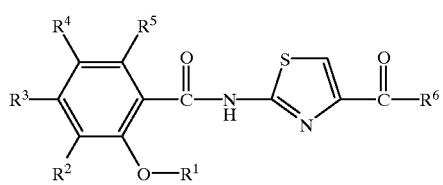

(1)

wherein R$^1$ represents a substituted or unsubstituted lower alkyl group, a substituted or unsubstituted allyl group, or a substituted or unsubstituted tetrahydropyranyl group; and R$^2$, R$^3$, R$^4$, R$^5$, and R$^6$ have the same meanings as described above; with a secondary amine or a tertiary amine.

2. The process according to claim 1, wherein the secondary amine or the tertiary amine is an amine having an amino group to which a linear, branched, or a cyclic alkyl group is bonded.

3. The process according to claim 1 or 2, wherein R$^1$ is a substituted or unsubstituted lower alkyl group.

4. The process according to claim 1, wherein the reaction is performed in the presence of a polar solvent.

5. A process for producing a 2-hydroxybenzamide derivative represented by formula (5):

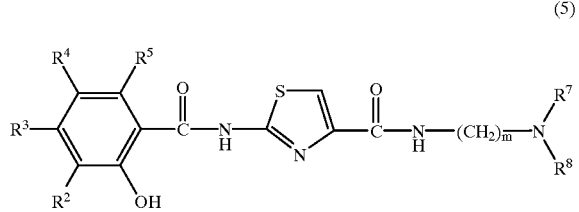

(5)

wherein R$^2$, R$^3$, and R$^4$ are the same or different and each independently represents a hydrogen atom, a hydroxy group, a lower alkyl group, a lower alkoxy group, a lower alkylsulfonyl group, a halogen atom, a nitro group, a cyano group, a mono- or di-lower alkylamino group, or a mono- or di-lower alkylcarbonylamino group, or R$^2$ and R$^3$ may join to each other to form a methylenedioxy group; R$^5$ represents a hydrogen atom, a lower alkyl group, a lower alkylsulfonyl group, a halogen atom, a nitro group, a cyano group, a mono- or di-lower alkylamino group, or a mono- or di-lower alkylcarbonylamino group; R$^7$ and R$^8$ are the same or different and each independently represents a hydrogen atom or a lower alkyl group; and m represents an integer of 1–4 inclusive, which comprises: reacting a 2-substituted benzamide compound represented by formula (3):

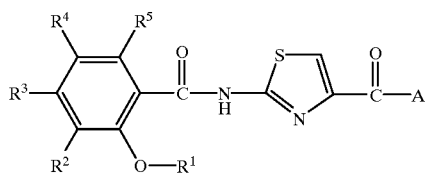

(3)

wherein R$^1$ represents a substituted or unsubstituted lower alkyl group, a substituted or unsubstituted allyl group, or a substituted or unsubstituted tetrahydropyranyl group; and R$^2$, R$^3$, R$^4$, and R$^5$ have the same meanings as described above; and A represents a hydroxy group or a lower alkoxy group; with a primary amine represented by formula (4):

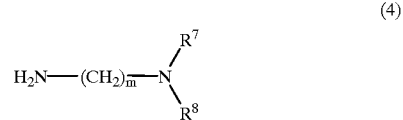

(4)

wherein m, R$^7$, and R$^8$ have the same meanings as described above, in the presence of a polar solvent.

6. The process according to claim 5, wherein the polar solvent is a sulfoxide-type solvent, an amide-type solvent, or a mixture thereof.

7. The process according to claim 3, wherein R$^1$ is substituted or unsubstituted benzyl.

8. The process according to claim 5, wherein R$^1$ as substituted or unsubstituted alkyl is substituted or unsubstituted benzyl.

* * * * *